US012722120B2

(12) United States Patent
Matsui et al.

(10) Patent No.: US 12,722,120 B2
(45) Date of Patent: Sep. 1, 2026

(54) CONCENTRATION APPARATUS AND CONCENTRATION METHOD

(71) Applicant: Yokogawa Electric Corporation, Tokyo (JP)

(72) Inventors: Yasuhiro Matsui, Musashino (JP); Kentaro Inoue, Musashino (JP); Hiroyuki Katayama, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 480 days.

(21) Appl. No.: 18/274,490

(22) PCT Filed: Nov. 25, 2021

(86) PCT No.: PCT/JP2021/043281
§ 371 (c)(1),
(2) Date: Jul. 27, 2023

(87) PCT Pub. No.: WO2022/163104
PCT Pub. Date: Aug. 4, 2022

(65) Prior Publication Data

US 2024/0316500 A1 Sep. 26, 2024

(30) Foreign Application Priority Data

Jan. 29, 2021 (JP) ................................ 2021-013736

(51) Int. Cl.
*B01D 61/18* (2006.01)
*B01D 61/22* (2006.01)
(Continued)

(52) U.S. Cl.
CPC ............ *B01D 61/18* (2013.01); *B01D 61/22* (2013.01); *B01D 69/02* (2013.01); *C02F 1/44* (2013.01);
(Continued)

(58) Field of Classification Search
CPC ........ B01D 61/18; B01D 61/22; B01D 69/02; B01D 2313/18; B01D 2313/243;
(Continued)

(56) References Cited

U.S. PATENT DOCUMENTS

2007/0187261 A1* 8/2007 Field .................. A47L 11/4083 205/742
2008/0237142 A1 10/2008 Carpenter et al.
(Continued)

FOREIGN PATENT DOCUMENTS

JP 62-79358 A 4/1987
JP 2005-177743 A 7/2005
JP 2012-87098 A 5/2012

OTHER PUBLICATIONS

English translation of Japanese Patent Application No. 2012-087098 A (2012).*

(Continued)

*Primary Examiner* — John Kim
(74) *Attorney, Agent, or Firm* — RANKIN, HILL & CLARK LLP

(57) ABSTRACT

A concentration apparatus including a negatively charged membrane, a sample water supply, a first solenoid valve on a flow path from the sample water supply to the negatively charged membrane, an acidic solution storage tank storing an acidic solution, a second solenoid valve on a flow path from the acidic solution storage tank to the negatively charged membrane, an alkaline solution storage tank storing an alkaline solution, a third solenoid valve on a flow path from the alkaline solution storage tank to the negatively charged membrane, an outlet to discharge fluid, a fourth solenoid valve and a first suction pump each on a flow path from the negatively charged membrane to the outlet, a collection container in which fluid is collected, a fifth solenoid valve on a flow path from the negatively charged
(Continued)

membrane to the collection container, and a controller that controls opening and closing of the solenoid valves.

11 Claims, 11 Drawing Sheets

(51) Int. Cl.
*B01D 69/02* (2006.01)
*C02F 1/44* (2023.01)
*C12M 1/00* (2006.01)
*C12M 1/02* (2006.01)
*C12N 1/02* (2006.01)
*G01N 1/40* (2006.01)

(52) U.S. Cl.
CPC ................. *C12M 1/00* (2013.01); *C12N 1/02* (2013.01); *G01N 1/4005* (2013.01); *B01D 2313/18* (2013.01); *B01D 2313/243* (2013.01); *B01D 2313/502* (2022.08); *B01D 2313/70* (2022.08); *B01D 2325/14* (2013.01); *B01D 2325/42* (2013.01)

(58) Field of Classification Search
CPC .......... B01D 2313/502; B01D 2313/70; B01D 2325/14; B01D 2325/42; C02F 1/44; C12M 1/00; C12N 1/02; G01N 1/4005
See application file for complete search history.

(56) References Cited

U.S. PATENT DOCUMENTS

2016/0090617 A1 3/2016 Gallardo
2023/0391645 A1 * 12/2023 Miyauchi ........... G01N 33/1826

OTHER PUBLICATIONS

Australian Office Action dated Sep. 15, 2025 for Australian Patent Application No. 2021424314.
Indian Office Action dated Nov. 12, 2025 for Indian Patent Application No. 202317049745.
Katayama et al., "Development of a Virus Concentration Method and Its Application to Detection of Enterovirus and Norwalk Virus from Coastal Seawater", Applied Environmental Microbiology, 2002, vol. 68, No. 3, pp. 1033-1039; Cited in International Search Report (ISR) dated Dec. 27, 2022 filed in Feb. 1, 2022 and Japanese Office Action (JPOA).

* cited by examiner

FIG. 1
Prior Art 100
120
CONTROLLER
101
SECOND SUCTION PUMP
104
114
V6
110
108
ALKALINE SOLUTION STORAGE TANK
111c
V3
111
102
NEGATIVELY CHARGED MEMBRANE
113b
V5
V4
113a
V2
ACID SOLUTION STORAGE TANK
111a
113
FIRST SUCTION PUMP
V1
111b
107
PRESSURIZATION TANK
S
109
103
M3
114
112
M2
P2
112a
SAMPLE WATER SUPPLY
M1
112b
P1
106
MIXING SOLUTION STORAGE TANK
105

*FIG. 11*

| | FIRST SOLENOID VALVE | SECOND SOLENOID VALVE | THIRD SOLENOID VALVE | FOURTH SOLENOID VALVE | FIFTH SOLENOID VALVE | SIXTH SOLENOID VALVE | FIRST PUMP P1 | SECOND PUMP P2 | FIRST FLOW METER M1 | SECOND FLOW METER M2 | THIRD FLOW METER M3 | PRESSURE SENSOR S | FIRST SUCTION PUMP 103 | SECOND SUCTION PUMP 104 |
|---|---|---|---|---|---|---|---|---|---|---|---|---|---|---|
| FIRST STEP | OPEN | CLOSED | CLOSED | OPEN | CLOSED | CLOSED | on | on | on | on | on | on | on | off |
| SECOND STEP | CLOSED | OPEN | CLOSED | OPEN | CLOSED | CLOSED | off | off | off | off | on | off | on | off |
| THIRD STEP | CLOSED | CLOSED | OPEN | CLOSED | CLOSED | CLOSED | off | off | off | off | off | off | off | off |
| FOURTH STEP | CLOSED | CLOSED | CLOSED | CLOSED | CLOSED | OPEN | off | off | off | off | off | off | off | on |
| FIFTH STEP | CLOSED | CLOSED | CLOSED | CLOSED | OPEN | CLOSED | off | off | off | off | off | off | off | off |

CONCENTRATION APPARATUS AND CONCENTRATION METHOD

CROSS-REFERENCE TO RELATED APPLICATION

The present application claims priority to and the benefit of Japanese Patent Application No. 2021-013736 filed Jan. 29, 2021, the entire contents of which are incorporated herein by reference.

TECHNICAL FIELD

The present disclosure relates to a concentration apparatus and a concentration method.

BACKGROUND

Microorganisms such as bacteria and viruses are generally negatively charged in neutral to alkaline waters and positively charged in acidic waters. Conventionally, methods of capturing microorganisms from water using this property are known. For example, Non-Patent Literature (NPL) 1 describes a negatively charged membrane method, which uses a negatively charged membrane to capture microorganisms from water.

CITATION LIST

Non-Patent Literature

NPL 1: Katayama et al, "Development of a Virus Concentration Method and Its Application to Detection of Enterovirus and Norwalk Virus from Coastal Seawater", Appl Environ Microbiol, March 2002, Vol. 68, No. 3, p. 1033-1039

SUMMARY

Technical Problem

However, detecting viruses in water by applying the negatively charged membrane method is not easy in water treatment infrastructure such as water purification plants, sewage treatment plants, water reclamation facilities or seawater desalination facilities, for example. For example, when trying to implement the negatively charged membrane method at a water treatment infrastructure site, workers need to assemble onsite the specialized equipment for the processing by the negatively charged membrane method, which requires workers to be arranged, as well as time and effort. Further, when sample water is collected at the water treatment infrastructure site and then processed by the negatively charged membrane method in a laboratory away from the water treatment infrastructure site, additional tools such as containers, and transportation work, are required to properly store and transport the sample water to the laboratory. In this case, the water sampling site and the laboratory where the negatively charged membrane is processed are separated, and therefore changing a policy of use of the negatively charged membrane method according to the sampling conditions of the sample water at the water treatment infrastructure facility may be difficult. Further, the operation of equipment for processing by the negatively charged membrane method has to be done by workers and is therefore a burden on workers.

It would be helpful to provide a concentration apparatus and a concentration method that improve the convenience of processing by the negatively charged membrane method.

Solution to Problem

A concentration apparatus according to at least one embodiment comprises: a negatively charged membrane that is negatively charged; a sample water supply disposed upstream of the negatively charged membrane and operable to supply sample water; a first solenoid valve disposed on a flow path from the sample water supply to the negatively charged membrane; an acidic solution storage tank disposed upstream of the negatively charged membrane in parallel with the sample water supply and storing an acidic solution; a second solenoid valve disposed on a flow path from the acidic solution storage tank to the negatively charged membrane; an alkaline solution storage tank disposed upstream of the negatively charged membrane in parallel with the sample water supply and the acidic solution storage tank and storing an alkaline solution; a third solenoid valve disposed on a flow path from the alkaline solution storage tank to the negatively charged membrane, an outlet disposed downstream of the negatively charged membrane and operable to discharge fluid externally; a fourth solenoid valve and a first suction pump each disposed on a flow path from the negatively charged membrane to the outlet; a collection container disposed downstream of the negatively charged membrane in parallel with the outlet and in which fluid is collected; a fifth solenoid valve disposed on a flow path from the negatively charged membrane to the collection container; and a controller that controls opening and closing of the first solenoid valve, the second solenoid valve, the third solenoid valve, the fourth solenoid valve, and the fifth solenoid valve. This automates the processing by the negatively charged membrane method in the concentration apparatus, thereby reducing the labor burden on workers when performing the processing by the negatively charged membrane method. Accordingly, the convenience of processing by the negatively charged membrane method may be improved.

According to an embodiment, the concentration apparatus further comprises a mixing solution storage tank disposed upstream of the first solenoid valve in parallel with the sample water supply that stores a mixing solution to be mixed with the sample water. This allows the sample water mixed with the mixing solution to be supplied to the negatively charged membrane.

According to an embodiment, the concentration apparatus further comprises: a first pump operable to pump the mixing solution downstream; and a second pump operable to pump the sample water downstream, wherein the controller controls the pumping by the first pump and the second pump. This allows the controller to automatically control an amount of the mixing solution mixed with the sample water.

According to an embodiment, the concentration apparatus further comprises a pressurization tank upstream of the first solenoid valve that stores the sample water supplied from the sample water supply. The sample water may be supplied to the negatively charged membrane at a defined pressure or more.

According to an embodiment, the controller is operable to execute a sequence of: a first step of opening the first solenoid valve and the fourth solenoid valve, closing the second solenoid valve, the third solenoid valve, and the fifth solenoid valve, and causing the first suction pump to be driven; a second step of opening the second solenoid valve and the fourth solenoid valve, closing the first solenoid valve, the third solenoid valve, and the fifth solenoid valve, and causing the first suction pump to be driven; and a third step of opening the third solenoid valve and closing the first solenoid valve, the second solenoid valve, the fourth solenoid valve and the fifth solenoid valve. This performs the processing by the negatively charged membrane method and purifies a microbial concentrate.

According to an embodiment, the concentration apparatus further comprises a second suction pump operable to create negative pressure inside the collection container. This allows negative pressure inside the collection container to draw a concentration into the collection container.

According to an embodiment, the controller is operable to execute a sequence of: a fourth step of closing the fifth solenoid valve and causing the second suction pump to be driven to create negative pressure inside the collection container; and a fifth step of closing the first solenoid valve, the second solenoid valve, the third solenoid valve, and the fourth solenoid valve and opening the fifth solenoid valve. This properly collects the microbial concentrate in the collection container in the processing by the negatively charged membrane method.

According to an embodiment, the concentration apparatus is configured as one integrated device. This allows the concentration apparatus to be transported to a location where processing by the negatively charged membrane method is required. This increases the convenience of processing by the negatively charged membrane method.

According to an embodiment, the concentration apparatus is configured as an integrated device by being entirely housed inside an enclosure. This facilitates transportation of the concentration apparatus and protects each mechanism inside the concentration apparatus.

According to an embodiment, the enclosure is provided with a handle that is graspable by a user. This allows a user to grasp the handle and carry the concentration apparatus.

According to an embodiment, the concentration apparatus further comprises wheels. This allows the concentration apparatus to be transported by traveling on wheels on the ground.

A concentration method according to at least one embodiment is executed by a concentration apparatus comprising: a negatively charged membrane that is negatively charged; a sample water supply disposed upstream of the negatively charged membrane and operable to supply sample water; a first solenoid valve disposed on a flow path from the sample water supply to the negatively charged membrane; an acidic solution storage tank disposed upstream of the negatively charged membrane in parallel with the sample water supply and storing an acidic solution; a second solenoid valve disposed on a flow path from the acidic solution storage tank to the negatively charged membrane; an alkaline solution storage tank disposed upstream of the negatively charged membrane in parallel with the sample water supply and the acidic solution storage tank and storing an alkaline solution; a third solenoid valve disposed on a flow path from the alkaline solution storage tank to the negatively charged membrane: an outlet disposed downstream of the negatively charged membrane and operable to discharge fluid externally; a fourth solenoid valve and a first suction pump each disposed on a flow path from the negatively charged membrane to the outlet; a collection container disposed downstream of the negatively charged membrane in parallel with the outlet and in which fluid is collected; and a fifth solenoid valve disposed on a flow path from the negatively charged membrane to the collection container, the concentration method comprising: a first step of opening the first solenoid valve and the fourth solenoid valve, closing the second solenoid valve, the third solenoid valve, and the fifth solenoid valve, and causing the first suction pump to be driven; a second step of opening the second solenoid valve and the fourth solenoid valve, closing the first solenoid valve, the third solenoid valve, and the fifth solenoid valve, and causing the first suction pump to be driven; and a third step of opening the third solenoid valve and closing the first solenoid valve, the second solenoid valve, the fourth solenoid valve and the fifth solenoid valve. This automates the processing by the negatively charged membrane method in the concentration apparatus, thereby reducing the labor burden on workers when performing the processing by the negatively charged membrane method. Accordingly, the convenience of processing by the negatively charged membrane method may be improved.

Advantageous Effect

According to the present disclosure, a concentration apparatus and a concentration method that improve the convenience of processing by the negatively charged membrane method are provided.

BRIEF DESCRIPTION OF THE DRAWINGS

In the Accompanying Drawings:

FIG. 1 is a schematic diagram for explanation of a Comparative Example of equipment capable of performing processing by a negatively charged membrane method;

FIG. 11 illustrates functional parts controlled by a controller in each step of the processing of the negatively charged membrane method executed by the concentration apparatus illustrated in FIG. 5.

DETAILED DESCRIPTION

Figure 2:
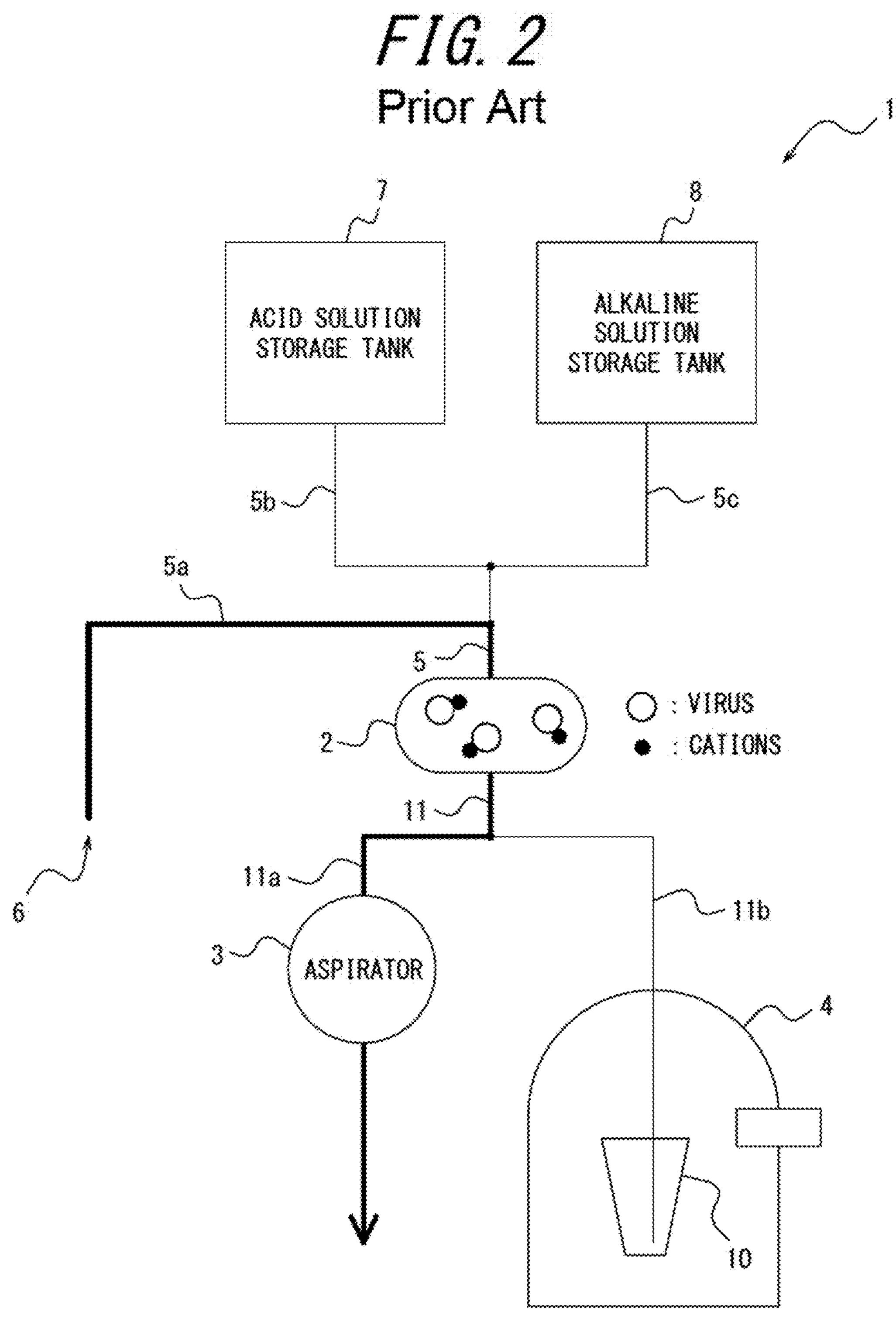
FIG. 2 is a schematic diagram for explanation of a processing step of the negatively charged membrane method executed via the equipment illustrated in FIG. 1.

An embodiment of the present disclosure is described below with reference to the drawings.

First, a Comparative Example is described of equipment that purifies concentrated solutions of microorganisms such as bacteria and viruses by a negatively charged membrane method. As an example, the present disclosure describes purification of a virus concentrate, but similar equipment and methods may be applied to other particulates such as bacteria. Microorganisms such as bacteria and viruses are negatively charged in neutral to alkaline waters. Sample water in which the processing of the negatively charged membrane method is performed is neutral to alkaline, and therefore such microorganisms are negatively charged in the sample water.

Figure 1:
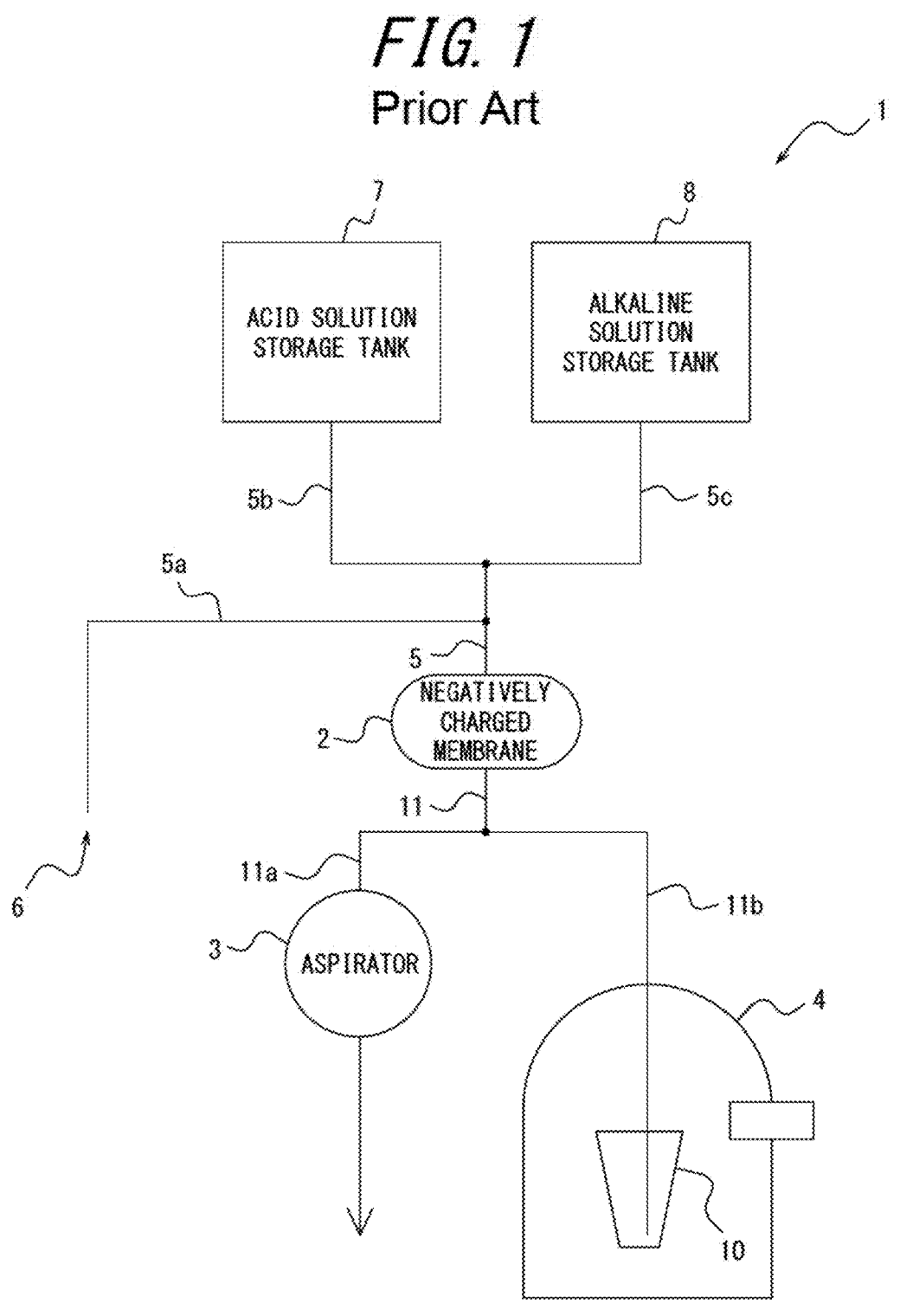

FIG. 1 is a schematic diagram for explanation of the Comparative Example of the equipment capable of performing processing by the negatively charged membrane method. As illustrated in FIG. 1, equipment 1 of the Comparative Example includes a negatively charged membrane 2, an aspirator 3, and a suction bottle 4. In FIG. 1, solid lines joining each component indicate piping through which fluid flows.

The negatively charged membrane 2 is a negatively charged membrane, for example, a mixed cellulose membrane manufactured by Millipore Corporation (hereinafter also referred to simply as "HA membrane") may be used. The negatively charged membrane 2 has pores able to capture viruses and allow molecules that make up a fluid, such as water molecules, to pass through. The pore diameter of the pores in the negatively charged membrane 2 may be determined according to the viruses and the like to be captured by the negatively charged membrane 2.

A pipe 5 is provided upstream of the negatively charged membrane 2 to supply fluid. In the Comparative Example illustrated in FIG. 1, three different pipes 5*a*, 5*b*, and 5*c* are manually reconnected for each step, and different fluids are supplied to the negatively charged membrane 2 via the pipe 5. Instead of the pipes Sa, 5*b*, and Sc being reconnected to the pipe 5, different fluids may be supplied to the negatively charged membrane 2 via the pipe 5 by changing a solution fed into the pipe 5.

Of the three pipes Sa, 5*b*, and Sc, a first pipe Sa connects the pipe 5 to a sample water supply port 6. From the sample water supply port 6, sample water that may contain a virus is supplied to the first pipe 5*a*. The sample water supply port 6 may be supplied with a defined solution mixed with sample water taken from a water treatment infrastructure facility. The defined solution may be, for example, a magnesium chloride solution. As the defined solution, an appropriate solution may be used depending on properties of the sample water. Further, the defined solution need not be used, depending on the properties of the sample water.

Of the three pipes 5*a*, 5*b*, and 5*c*, a second pipe Sb connects the pipe 5 to an acidic solution storage tank 7 where an acidic aqueous solution is stored. The acidic aqueous solution is supplied to the second pipe 5*b* from the acidic solution storage tank 7. The acidic aqueous solution is described herein as a sulfuric acid solution as an example, but is not limited to this.

Of the three pipes 5*a*, 5*b*, and 5*c*, a third pipe 5*c* connects the pipe 5 to an alkaline solution storage tank 8 where an alkaline aqueous solution is stored. The alkaline aqueous solution is supplied to the third pipe 5*c* from the alkaline solution storage tank 8. The alkaline aqueous solution is described herein as a sodium hydroxide aqueous solution as an example, but is not limited to this.

Fluid is supplied to the negatively charged membrane 2 via the pipe 5 from each of the three pipes 5*a*, 5*b*, and 5*c* connected in a given step. Only one of the sample water, the acidic aqueous solution, and the alkaline aqueous solution is supplied to the negatively charged membrane 2 at a given time. In other words, the pipes 5*a*, 5*b* and Sc are manually reconnected for each step so that two or more of the sample water, the acidic aqueous solution, and the alkaline aqueous solution are not supplied at the same timing.

The aspirator 3 is disposed downstream of the negatively charged membrane 2. The aspirator 3 draws in the fluid supplied to the negatively charged membrane 2 by creating a reduced pressure condition. In the Comparative Example illustrated in FIG. 1, in cases where the sample water and the acidic aqueous solution are supplied to the negatively charged membrane 2, the aspirator 3 is driven and fluid is drawn into the aspirator 3 and discharged externally.

The suction bottle 4 is disposed downstream of the negatively charged membrane 2 and in parallel with the aspirator 3. The suction bottle 4 draws in the fluid supplied to the negatively charged membrane 2 by creating a reduced pressure condition and collects the fluid in a concentrated fluid collection container 10 provided internally. In the Comparative Example illustrated in FIG. 1, when the alkaline aqueous solution is supplied to the negatively charged membrane 2, the fluid is drawn into the suction bottle 4 and collected in the concentrated fluid collection container 10.

Figure 3:
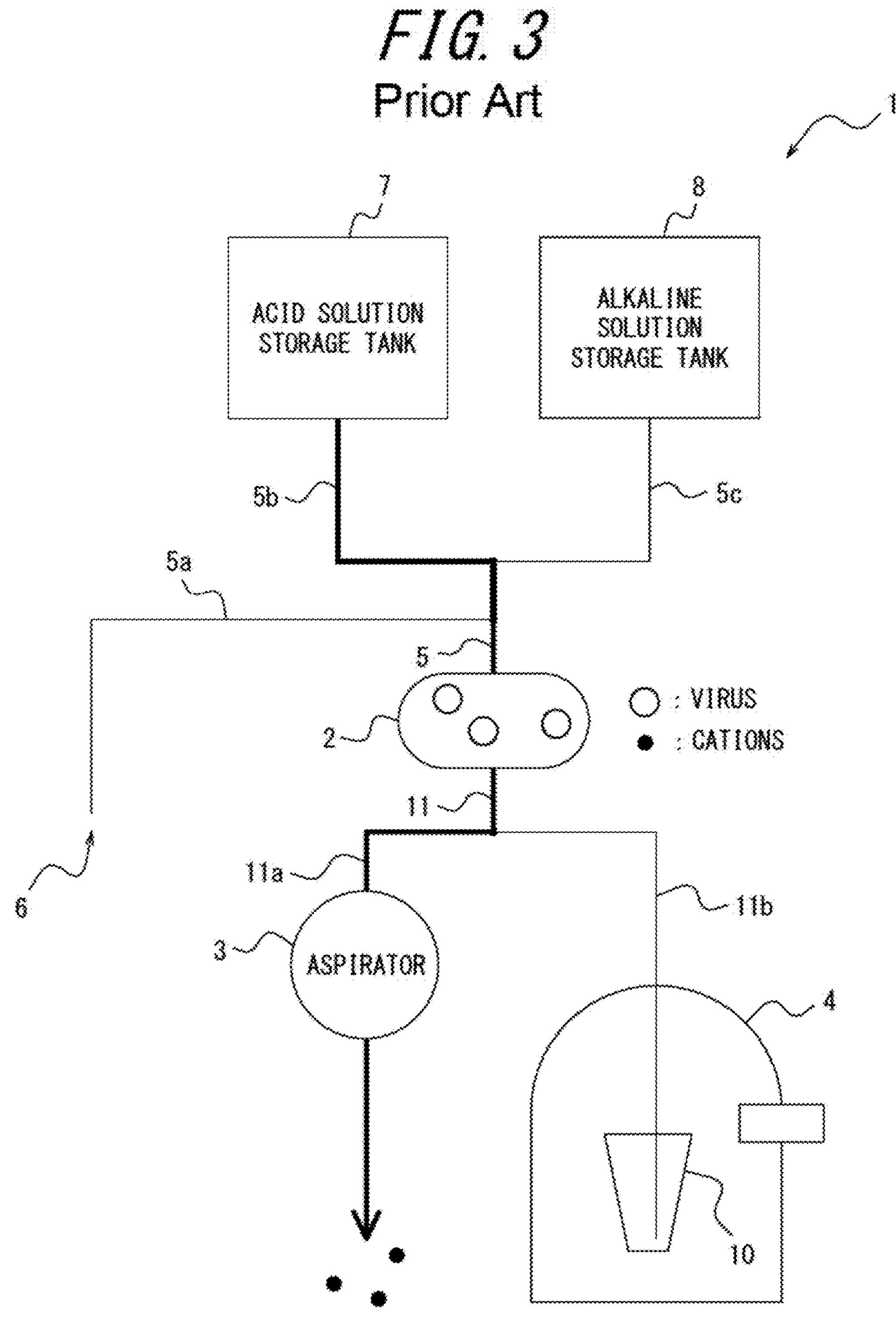
FIG. 3 is a schematic diagram for explanation of a processing step of the negatively charged membrane method executed via the equipment illustrated in FIG. 1.
Figure 4:
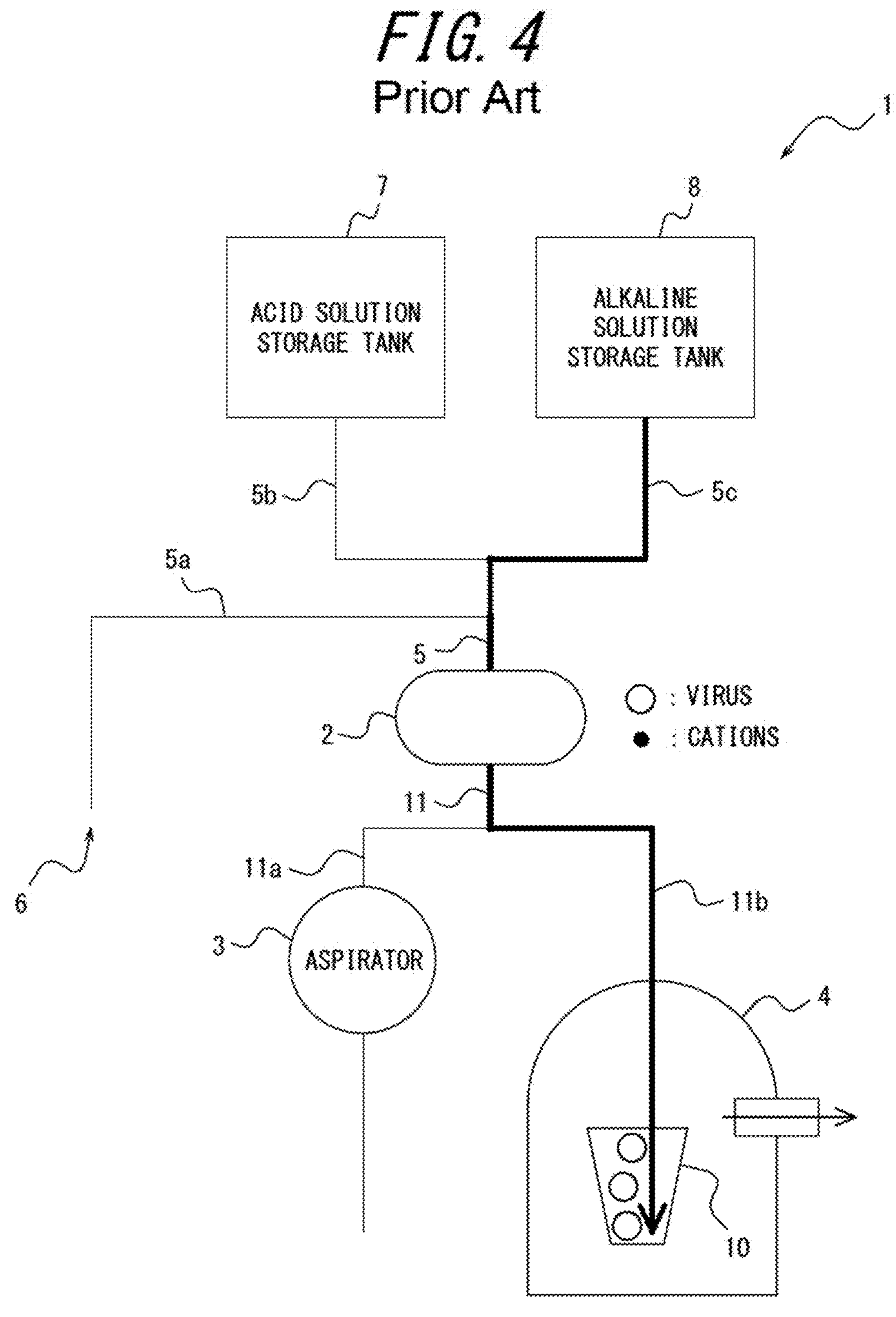
FIG. 4 is a schematic diagram for explanation of a processing step of the negatively charged membrane method executed via the equipment illustrated in FIG. 1.

The following is a description of a processing method according to the negatively charged membrane method using the equipment of the Comparative Example illustrated in FIG. 1. FIG. 2 through FIG. 4 are schematic diagrams for explanation of processing steps of the negatively charged membrane method performed by the equipment 1 illustrated in FIG. 1. Bold lines in FIG. 2 through FIG. 4 indicate fluid flow.

First, the first pipe Sa is connected to the pipe 5 and the aspirator 3 is driven to supply sample water from the sample water supply port 6 to the negatively charged membrane 2 via the first pipe 5*a*, as illustrated in FIG. 2. As the sample water passes through the negatively charged membrane 2, cations in the sample water have a positive charge and are therefore captured by the negatively charged membrane 2. Further, viruses in the sample water are larger than the pores of the negatively charged membrane 2 and are therefore captured by the negatively charged membrane 2. As the negatively charged membrane 2, one capable of capturing viruses at this time is used. For example, an HA membrane having a pore size of 0.45 μm and a diameter of 13 mm to 90 mm may be used as the negatively charged membrane 2. The sample water with captured cations and viruses is drained by the aspirator 3 through a pipe 11 and a pipe 11*a* disposed downstream of the negatively charged membrane 2.

Next, the second pipe 5*b* is connected to the pipe 5 instead of the first pipe 5*a*, and the aspirator 3 is driven to supply the sulfuric acid solution from the acidic solution storage tank 7 through the second pipe 5*b* to the negatively charged membrane 2, as illustrated in FIG. 3. This results in acid cleaning of the negatively charged membrane 2. In other words, by supplying the sulfuric acid solution to the negatively charged membrane 2 and flowing downstream via the aspirator 3, the cations captured in the negatively charged membrane 2 are stripped from the negatively charged membrane 2 and drained with the sulfuric acid solution through the pipe 11 and the pipe 11*a*. The sulfuric acid solution may be any acid washing solution, for example, 0.5 mM sulfuric acid solution at pH 3.0. The sulfuric acid solution may be supplied in an appropriate volume, for example, one-tenth the volume of the supplied sample water. Acid washing leaves the negatively charged membrane 2 with viruses adhering thereto.

Then, the third pipe 5*c* is connected to the pipe 5 instead of the second pipe 5*b*, and sodium hydroxide aqueous solution is supplied to the negatively charged membrane 2 from the alkaline solution storage tank 8 through the third pipe 5*c*, as illustrated in FIG. 4. As a result, the negatively charged virus captured by the negatively charged membrane 2 is stripped from the negatively charged membrane 2 and flows with the sodium hydroxide aqueous solution through the pipe 11 and the pipe 11*b* to the suction bottle 4 and is collected in the concentrated solution collection container 10. The sodium hydroxide aqueous solution may be any solution from which viruses may be recovered, for example, a 1.0 mM sodium hydroxide aqueous solution at pH 10.5 to pH 10.8. The sodium hydroxide aqueous solution may be supplied in an appropriate volume, for example, 1 ml to 10 ml.

The concentrated solution collection container 10 is preferably pre-filled with a solution to neutralize the sodium hydroxide aqueous solution from which the virus is collected. For example, the concentrated solution collection container 10 is preferably pre-filled with 5 μl to 50 μl of 0.2 N sulfuric acid solution and 10 μl to 100 μl of pH 8.0 buffer solution.

Thus, the processing described with reference to FIG. 2 through FIG. 4 may purify a virus in the sample water into a concentrated solution collection container 10 by performing the negatively charged membrane method using the equipment 1.

The negatively charged membrane method using the equipment 1 described above may be applied to water treatment infrastructure such as water purification plants, sewage treatment plants, water reclamation facilities, seawater desalination facilities, and the like. However, when applying the negatively charged membrane method using the equipment 1 described above to water treatment infrastructure, for example, when the negatively charged membrane method is to be implemented at the water treatment infrastructure site, workers need to assemble the equipment 1 to be used in the treatment on site. Further, when using the equipment 1 to perform the processing according to the negatively charged membrane method, workers need to reconnect the piping as described above. Therefore, arranging for skilled workers capable of assembling and disassembling the equipment 1 and reconnecting the piping is necessary. Further, time and effort are required to assemble and disassemble the equipment 1. When the water treatment infrastructure to be sampled is located outdoors, additional equipment may be required, which could require additional time and effort. Further, workers must be on site at all times to respond to problems on site. Further, the number of people and the amount of time they have access to the facility may be limited at a water treatment infrastructure site, making it difficult to dispatch a large number of workers or to allow the workers to spend long periods of time working or taking water samples.

Further, when sample water is collected at the water treatment infrastructure site and then processed by the negatively charged membrane method in a laboratory away from the water treatment infrastructure site, additional tools such as containers, and transportation work, are required to properly store and transport the sample water to the laboratory. In this case, the water sampling site and the laboratory where the negatively charged membrane is processed are separated, and therefore changing a policy of use of the negatively charged membrane method according to the sampling conditions of the sample water at the water treatment infrastructure facility may be difficult.

Although the negatively charged membrane method is able to capture microorganisms such as bacteria and viruses with a high recovery rate, the work described in FIG. 2 through FIG. 4 has to be performed by workers using the equipment 1. This places a heavy burden on the workers. Further, accurately performing the tasks described with reference to FIG. 2 through FIG. 4 is not easy, and is complicated. In particular, when the need to control water quality arises during an emergency or unusual situation in the water treatment infrastructure, personnel who are not necessarily familiar with the operation of the equipment 1 that performs the negatively charged membrane method may have to operate the equipment 1, which may result in a lack of accurate work, and thus microorganisms might not be properly recovered.

Further, in practice, when managing the operation and quality of water treatment infrastructure, the facilities and environmental conditions may not always be suitable for the negatively charged membrane method, and being able to implement the negatively charged membrane method more conveniently is desirable. Due to the complicated nature of the processing by the negatively charged membrane method, especially in a water treatment infrastructure with strict entry restrictions, there is also a problem that the negatively charged membrane method might only be performed by taking only a single sample.

The following is a description of a concentration apparatus that is able to solve the problems described above.

Figure 5:
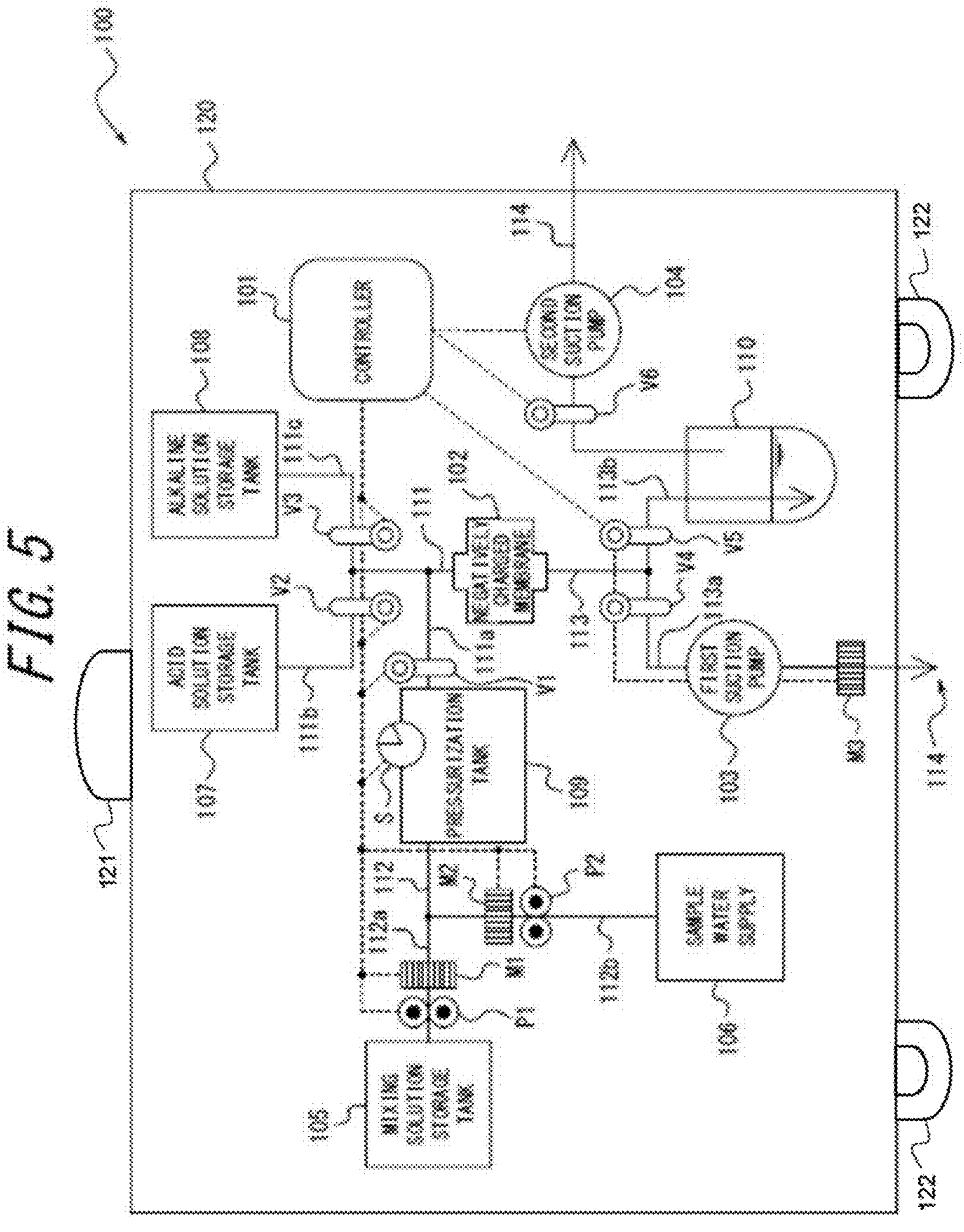
FIG. 5 is a schematic diagram of a concentration apparatus according to an embodiment of the present disclosure.

FIG. 5 is a schematic diagram of a concentration apparatus 100 according to an embodiment of the present disclosure. As illustrated in FIG. 5, the concentration apparatus 100 includes a controller 101, a negatively charged membrane 102, a first suction pump 103, a second suction pump 104, a mixing solution storage tank 105, a sample water supply 106, an acidic solution storage tank 107, an alkaline solution storage tank 108, a pressurization tank 109, and a concentrated solution collection container 110. In FIG. 5, solid lines joining each component indicate piping through which fluid flows. As illustrated in FIG. 5, the concentration apparatus 100 further includes a first pump P1, a second pump P2, a first flow meter M1, a second flow meter M2, a third flow meter M3, a pressure sensor S, a first solenoid valve V1, a second solenoid valve V2, a third solenoid valve V3, a fourth solenoid valve V4, a fifth solenoid valve V5, and a sixth solenoid valve V6. In FIG. 5, dashed lines joining each component indicate transmission paths of signals to be sent to and from the controller 101.

The controller 101 is a processor that controls and manages the concentration apparatus 100 overall, including each component included in the concentration apparatus 100. The controller 101 controls the first suction pump 103, the second suction pump 104, the first pump P1, the second pump P2, the first solenoid valve V1, the second solenoid valve V2, the third solenoid valve V3, the fourth solenoid valve V4, the fifth solenoid valve V5, and the sixth solenoid valve V6 by sending control signals. The controller 101 obtains information about measured flow rates from the first flow meter M1, the second flow meter M2, and the third flow meter M3, as well as information about measured pressure from the pressure sensor S. Processing executed by the controller 101 may be designed using a microcomputer, Raspberry Pi, Arduino, or the like, but is not limited to these examples. The controller 101 includes a processor such as a central processing unit (CPU) that executes a program that defines control steps. The program to be executed by the processor is stored, for example, in an internal or external storage medium or the like of the concentration apparatus 100.

The negatively charged membrane 102 is a negatively charged membrane, for example, an HA membrane may be used. The negatively charged membrane 102 may be constructed in the same way as the negatively charged membrane 2 of the Comparative Example illustrated in FIG. 1.

Upstream of the negatively charged membrane 102 is an upstream pipe 111 for supplying fluid. Three different pipes, a first pipe 111*a*, a second pipe 111*b*, and a third pipe 111*c*, are connected to the upstream pipe 111, and different fluids are supplied from these three pipes 111*a*, 111*b*, and 111*c*, respectively, to the negatively charged membrane 2 via the upstream pipe 111.

The first pipe 111*a* connects the upstream pipe 111 to the pressurization tank 109. The first solenoid valve V1 is provided to the first pipe 111*a*. The first solenoid valve V1 is disposed on a flow path from the sample water supply 106 to the negatively charged membrane 102 and controls the supply of fluid stored in the pressurization tank 109 to the negatively charged membrane 102. Upstream of the pressurization tank 109 are the mixing solution storage tank 105 and the sample water supply 106.

The mixing solution storage tank 105 stores a solution to be mixed with sample water supplied from the sample water supply 106 (hereinafter also simply referred to as "mixing solution"). The mixing solution may be magnesium chloride solution, but is not limited to this example. As the defined solution, an appropriate solution may be used depending on properties of the sample water. According to the present embodiment, the mixing solution is described below as a magnesium chloride solution. A fourth pipe 112*a* is connected to the mixing solution storage tank 105, which supplies the magnesium chloride solution to a mixing pipe 112, which leads to the pressurization tank 109 via the fourth pipe 112*a*. The first pump P1 that controls the flow rate of the magnesium chloride solution and the first flow meter M1 that measures the flow rate of the fluid flowing inside the fourth pipe 112*a* are disposed in the fourth pipe 112*a*. Information about the flow rate measured by the first flow meter M1 is transmitted to the controller 101, which controls the pumping of liquid by the first pump P1 based on the obtained information about the flow rate.

The sample water supply 106 supplies sample water taken from a water treatment plant. The sample water supply 106 may be configured as a mechanism to supply sample water collected from a water treatment plant by hose, tube, or the like, and may be configured as a tank to store sample water collected at a water treatment plant. A fifth pipe 112*b* is connected to the sample water supply 106, and sample water is supplied via the fifth pipe 112*b* to the mixing pipe 112 leading to the pressurization tank 109. The second pump P2 that controls the flow rate of the sample water and the second flow meter M2 that measures the flow rate of the fluid flowing inside the fifth pipe 112*b* are disposed in the fifth pipe 112*b*. Information about the flow rate measured by the second flow meter M2 is transmitted to the controller 101, which controls the pumping of liquid by the second pump P2 based on the obtained information about the flow rate.

The first pump P1 and the second pump P2 are pumps able to pump fluid downstream. The first pump P1 and the second pump P2 may be, for example, Perista® Pumps (Perista is a registered trademark in Japan, other countries, or both) that pump liquid by squeezing a soft tube with rollers. By using the first pump P1 and the second pump P2, the amount of the mixing solution mixed with the sample water is automatically controlled by the controller 101.

The sample water and the magnesium chloride solution are simultaneously supplied to the mixing pipe 112, mixed in the mixing pipe 112, and supplied to the pressurization tank 109. The pressurization tank 109 is a tank for storing the solution in which the sample water and magnesium chloride solution are mixed (hereinafter also simply referred to as "post-mixing solution") The pressurization tank 109 is capable of hermetically storing the post-mixing solution at a pressure higher than atmospheric pressure. The pressure sensor S is attached to the pressurization tank 109. The pressure sensor S measures the pressure inside the pressurization tank 109 and sends information about the measured pressure to the controller 101.

The second pipe 111*b* connects the upstream pipe 111 to the acidic solution storage tank 107. The acidic solution storage tank 107 is a tank that stores an acidic aqueous solution (acidic solution). The acidic aqueous solution is described herein as a sulfuric acid solution as an example, but is not limited to this. The second solenoid valve V2 is provided in the second pipe 111*b*. The second solenoid valve V2 is disposed on the flow path from the acidic solution storage tank 107 to the negatively charged membrane 102 and controls the supply of the acidic aqueous solution stored in the acidic solution storage tank 107 to the negatively charged membrane 102.

The third pipe 111*c* connects the upstream pipe 111 to the alkaline solution storage tank 108. The alkaline solution storage tank 108 is a tank that stores an alkaline aqueous solution (alkaline solution). The alkaline aqueous solution is described herein as a sodium hydroxide aqueous solution as an example, but is not limited to this. The third solenoid valve V3 is provided in the third pipe 111*c*. The third solenoid valve V3 is disposed on the flow path from the alkaline solution storage tank 108 to the negatively charged membrane 102 and controls the supply of the alkaline aqueous solution stored in the alkaline solution storage tank 108 to the negatively charged membrane 102.

Downstream of the negatively charged membrane 102 is a downstream pipe 113 for discharging fluid that has passed through the negatively charged membrane 102. Two different pipes, a sixth pipe 113*a* and a seventh pipe 113*b*, are connected to the downstream pipe 113.

The sixth pipe 113*a* is provided with the fourth solenoid valve V4, the first suction pump 103, and the third flow meter M3. The sixth pipe 113*a* discharges fluid from an outlet 114. The fourth solenoid valve V4 is disposed on the flow path from the negatively charged membrane 102 to the outlet 114 and controls the discharge of fluid that has passed through the negatively charged membrane 102 from the sixth pipe 113*a*. The first suction pump 103 is a pump that draws fluid from the negatively charged membrane 102 to the sixth pipe 113*a* side. The first suction pump 103 includes, for example, an aspirator that draws in fluid by creating a reduced pressure condition. The third flow meter M3 measures the flow rate of fluid flowing in the sixth pipe 113*a*. Information about the flow rate measured by the third flow meter M3 is transmitted to the controller 101, which controls the drawing of fluid by the first suction pump 103 based on the obtained information about the flow rate.

The seventh pipe 113*b* is provided with the fifth solenoid valve V5 The seventh pipe 113*b* connects the downstream pipe 113 to the concentrated solution collection container 110. The fifth solenoid valve V5 is disposed on the flow path from the negatively charged membrane 102 to the concentrated solution collection container 110 and controls the drawing of fluid that has passed through the negatively charged membrane 102 into the concentrated solution collection container 110. The concentrated solution collection container 110 is a container that collects fluid (concentrated solution) containing the virus captured by the negatively charged membrane 102. The concentrated solution collection container 110 includes a hermetically sealable container.

The outlet 114 is attached to the concentrated solution collection container 110. The outlet 114 is provided with the sixth solenoid valve V6 and the second suction pump 104. The outlet 114 is arranged such that one end of the outlet 114 is disposed in the interior space of the concentrated solution collection container 110. The second suction pump 104 is a pump that draws gas from inside the concentrated solution collection container 110 and discharges externally. The sixth solenoid valve V6 controls the drawing of gas from the inside of the concentrated solution collection container 110 to the outside.

The concentration apparatus 100 is configured as a single integrated (packaged) device. The concentration apparatus 100 may be configured as an integrated device as a whole, with each functional part fixed to a structure formed using an L-shaped angle or other frame, for example.

The concentration apparatus 100 may be configured as an integrated device by being entirely housed inside an enclosure 120, such as a duralumin case, for example, as schematically illustrated in FIG. 5. The housing in the enclosure 120 facilitates transportation of the concentration apparatus 100 and protects each mechanism inside the concentration apparatus 100. The concentration apparatus 100 may further be provided with an electric power cable to obtain electric power from outside the enclosure 120. The concentration apparatus 100 may be provided with a battery or other electric power source inside the enclosure 120 that is able to supply electric power. The concentration apparatus 100 may be provided with a handle 121 on the outside of the enclosure 120 that is graspable by a user. By providing the concentration apparatus 100 with the handle 121, a user may grasp the handle 121 and carry the concentration apparatus 100.

The concentration apparatus 100 integrated by a frame or the enclosure 120 may be provided with wheels 122. The wheels 122 may be provided on the enclosure 120, for example. The wheels 122 allow a user to transport the concentration apparatus 100 by traveling on the wheels 122 on the ground.

The concentration apparatus 100 integrated by a frame or the enclosure 120 may be provided with wheels. The wheels may be provided on the enclosure 120, for example. The wheels allow a user to transport the concentration apparatus 100 by traveling on the wheels on the ground.

Next, processing steps of the negatively charged membrane method using the concentration apparatus 100 illustrated in FIG. 5 are described with reference to FIG. 6 through FIG. 11. FIG. 6 through FIG. 10 are schematic diagrams for explanation of steps of processing the negatively charged membrane method executed by the concentration apparatus 100. Bold lines in FIG. 6 through FIG. 10 indicate fluid flow. FIG. 11 illustrates a list of functional parts controlled by the controller 101 in each step of the processing of the negatively charged membrane method executed by the concentration apparatus 100. In FIG. 11, “open” indicates that the solenoid valve is open, and “closed” indicates that the solenoid valve is closed. In FIG. 11, “on” indicates that the first pump P1, the second pump P2, the first flow meter M1 through to the third flow meter M3, the pressure sensor S, the first suction pump 103 and the second suction pump 104 are driven, and “off” indicates that the first flow meter M1 through to the third flow meter M3, the pressure sensor S, the first suction pump 103, and second suction pump 104 are stopped.

The processing of the negatively charged membrane method by the concentration apparatus 100 is realized by control by the controller 101. In other words, in the concentration apparatus 100, the processing of the negatively charged membrane method is automated. Specifically, the controller 101 executes the processing of the negatively charged membrane method by controlling the first solenoid valve V1 through to the sixth solenoid valve V6, the first pump P1, the second pump P2, the first flow meter M1 through to the third flow meter M3, the pressure sensor S, the first suction pump 103 and the second suction pump 104.

Figure 6:
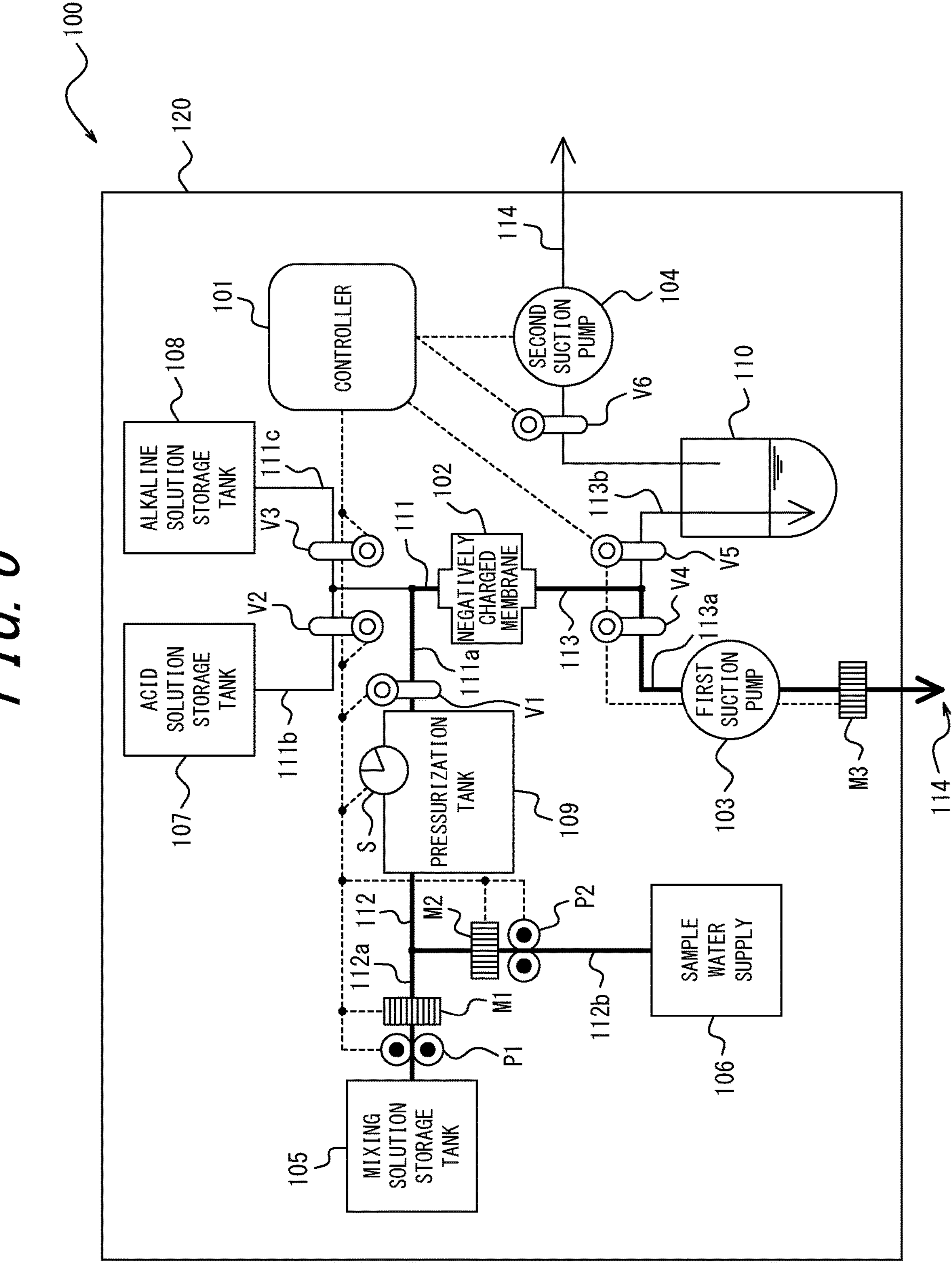
FIG. 6 is a schematic diagram for explanation of a first step of processing of a negatively charged membrane method executed by the concentration apparatus illustrated in FIG. 5.

FIG. 6 is a schematic diagram for explanation of a first step of the processing of the negatively charged membrane method executed by the concentration apparatus 100 illustrated in FIG. 5. In the first step, as illustrated in FIG. 11, the controller 101 opens the first solenoid valve V1 and the fourth solenoid valve V4 and closes the other solenoid valves. The controller 101 also causes the first pump P1, the second pump P2, the first flow meter M1 through to the third flow meter M3, the pressure sensor S, and the first suction pump 103 to be driven, and the second suction pump 104 to be stopped.

The controller 101 thereby obtains information about the flow rates of the fourth pipe 112*a* and the fifth pipe 112*b* from the first flow meter M1 and the second flow meter M2, respectively. The controller 101 controls the first pump P1 and the second pump P2 based on the information about the obtained flow rates.

In the first step, the first solenoid valve V1 and the fourth solenoid valve V4 are opened and the first suction pump 103 is driven, so that the sample water and the magnesium chloride solution are mixed in the mixing pipe 112 and supplied from the pressurization tank 109 to the negatively charged membrane 102 as illustrated in FIG. 6. The controller 101 is able to cause mixing of the sample water and the magnesium chloride solution in the mixing pipe 112 by coordinated control of the first flow meter M1, the second flow meter M2, the first pump P1, and the second pump P2.

The controller 101 obtains information about the pressure in the pressurization tank 109 from the pressure sensor S. When the controller 101 causes supply of a defined amount or more of the post-mixing solution mixed in the mixing pipe 112 to the negatively charged membrane 102, the controller 101 may cause pressurization of the pressurization tank 109 to supply the post-mixing solution to the negatively charged membrane 102. This allows the post-mixing solution to be supplied to the negatively charged membrane 102 at a defined pressure or more. When the specifications of the concentration apparatus 100 do not require pressurization of the post-mixing solution, the concentration apparatus 100 need not be provided with the pressurization tank 109.

The post-mixing solution mixed in the mixing pipe 112 is supplied to the negatively charged membrane 102, where cations and viruses in the solution are captured. The liquid from the negatively charged membrane 102, after the cations and virus have been captured, is discharged externally from the sixth pipe 113*a*. The flow rate of the discharged liquid is measured by the third flow meter M3, and information about the measured flow rate is transmitted to the controller 101. The controller 101 is able to control the suction amount of the first suction pump 103 based on the information about the obtained flow rate.

The controller 101 terminates the first step and transitions to a second step at an appropriately defined timing, for example, after a defined time has elapsed since the start of the first step, after a defined amount of fluid has been discharged in the first step, or the like.

Figure 7:
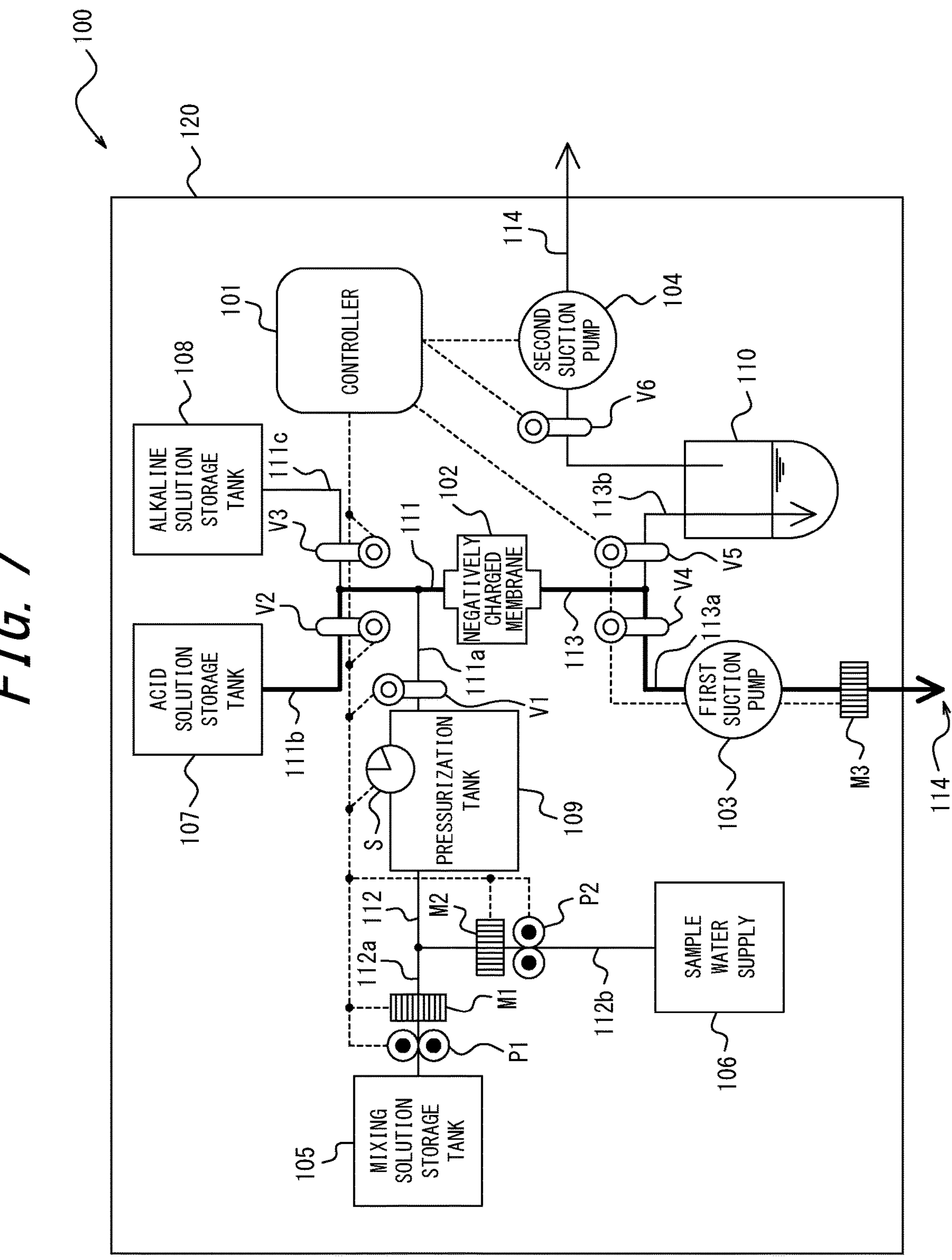
FIG. 7 is a schematic diagram for explanation of a second step of processing of the negatively charged membrane method executed by the concentration apparatus illustrated in FIG. 5.

FIG. 7 is a schematic diagram for explanation of the second step of the processing of the negatively charged membrane method executed by the concentration apparatus 100 illustrated in FIG. 5. In the second step, as illustrated in FIG. 11, the controller 101 opens the second solenoid valve V2 and the fourth solenoid valve V4 and closes the other solenoid valves. The controller 101 also causes the third flow meter M3 and the first suction pump 103 to be driven, while the first pump P1, the second pump P2, the first flow meter M1, the second flow meter M2, the pressure sensor S and the second suction pump 104 are stopped.

This supplies the sulfuric acid solution from the acidic solution storage tank 107 to the negatively charged membrane 102, as illustrated in FIG. 7. This results in acid cleaning of the negatively charged membrane 102, and the cations trapped in the negatively charged membrane 102 are stripped from the negatively charged membrane 2 and flow downstream with the sulfuric acid solution. The liquid after being acid washed is discharged externally from the sixth pipe 113*a*. The flow rate of the discharged liquid is measured by the third flow meter M3, and information about the measured flow rate is transmitted to the controller 101. The controller 101 is able to control the suction amount of the first suction pump 103 based on the information about the obtained flow rate.

After the controller 101 has caused external discharge of all supplied sulfuric acid solution in the second step, the controller 101 terminates the second step and transitions to a third step.

Figure 8:
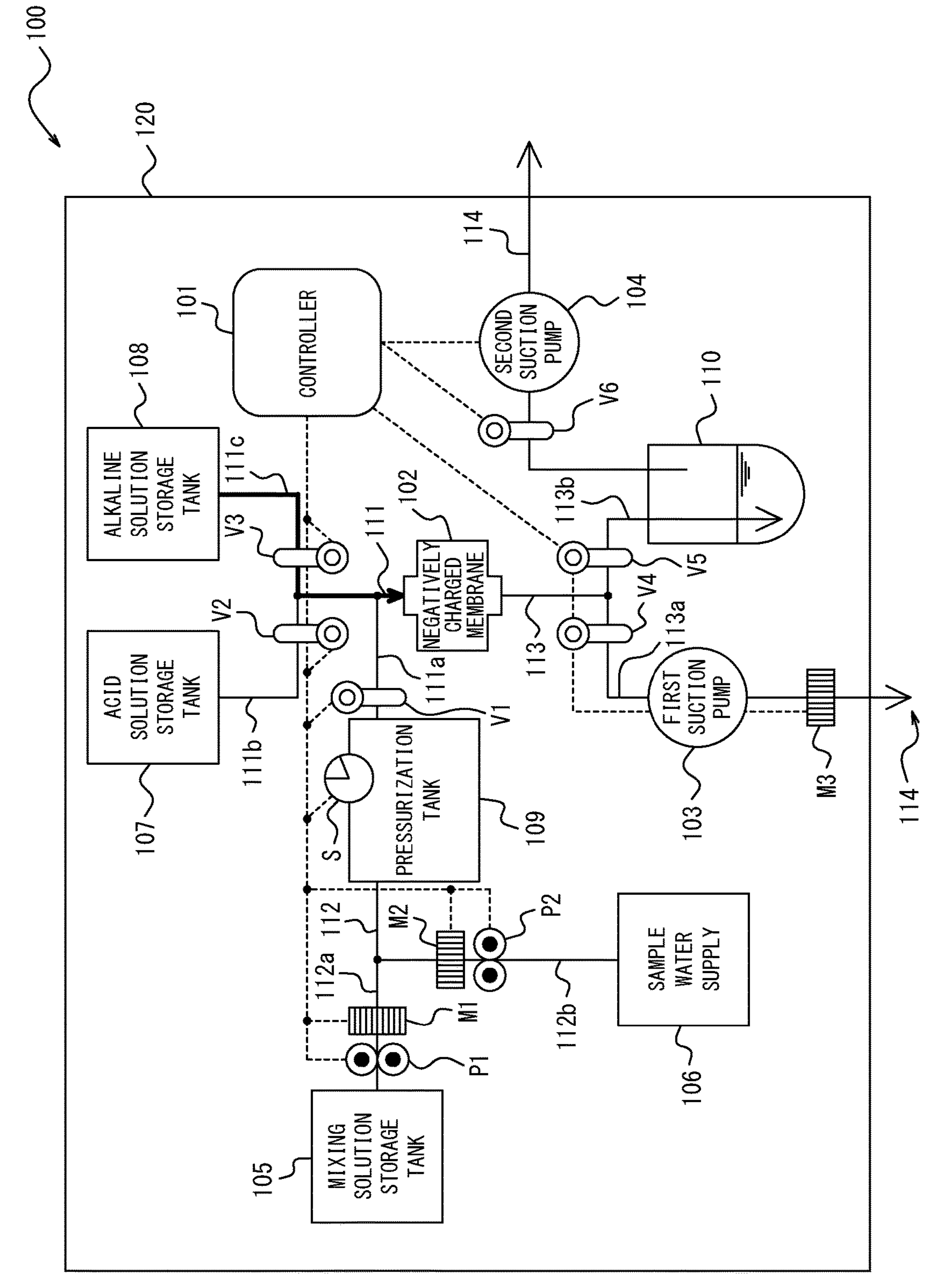
FIG. 8 is a schematic diagram for explanation of a third step of processing of the negatively charged membrane method executed by the concentration apparatus illustrated in FIG. 5.

FIG. 8 is a schematic diagram for explanation of the third step of the processing of the negatively charged membrane method executed by the concentration apparatus 100 illustrated in FIG. 5. In the third step, as illustrated in FIG. 11, the controller 101 opens the third solenoid valve V3 and closes the other solenoid valves. The controller 101 also causes the first pump P1, the second pump P2, the first flow meter M1 through to the third flow meter M3, the pressure sensor S, the first suction pump 103, and the second suction pump 104 to be stopped.

This supplies the sodium hydroxide aqueous solution from the acidic solution storage tank 107 to the negatively charged membrane 102, as illustrated in FIG. 8. The sodium hydroxide aqueous solution flows onto a membrane surface of the negatively charged membrane 102. The concentration apparatus 100 may be provided with a mechanism for venting air from piping at this time, as necessary. The sodium hydroxide aqueous solution is preferably supplied in an amount that becomes some millimeters thick on the negatively charged membrane 102.

When the controller 101 supplies the sodium hydroxide aqueous solution to the negatively charged membrane 102, the controller 101 terminates the third step and transitions to a fourth step.

Figure 9:
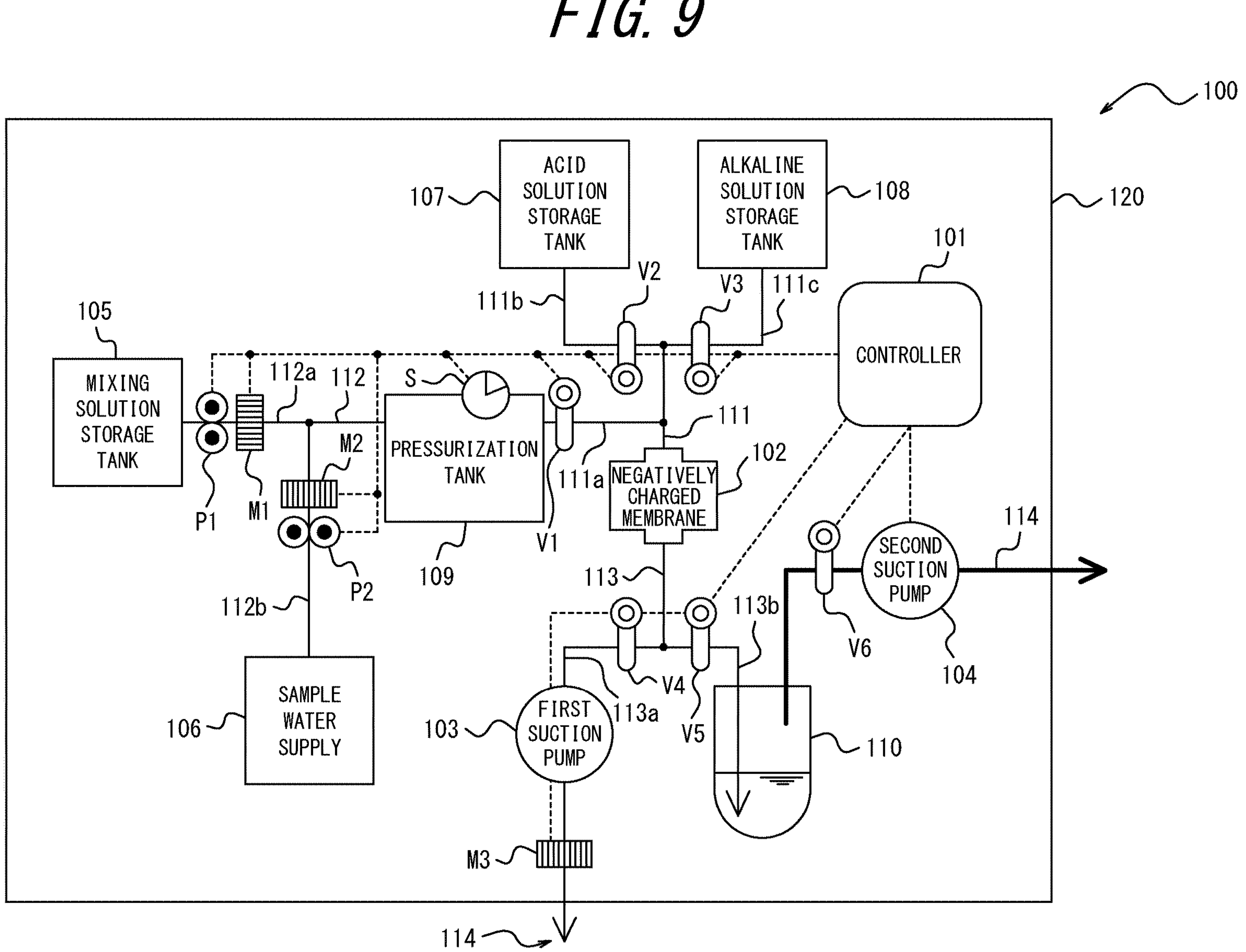
FIG. 9 is a schematic diagram for explanation of a fourth step of processing of the negatively charged membrane method executed by the concentration apparatus illustrated in FIG. 5.

FIG. 9 is a schematic diagram for explanation of the fourth step of the processing of the negatively charged membrane method executed by the concentration apparatus 100 illustrated in FIG. 5. In the fourth step, as illustrated in FIG. 11, the controller 101 opens the sixth solenoid valve V6 and closes the other solenoid valves. The controller 101 also causes the second suction pump 104 to be driven, and causes the first pump P1, the second pump P2, the first flow meter M1 through to the third flow meter M3, the pressure sensor S, and the first suction pump 103 to be stopped.

This causes gas to be discharged externally from the space inside the concentrated solution collection container 110, resulting in negative pressure inside the concentrated solution collection container 110.

The controller 101, for example, terminates the fourth step and transitions to a fifth step after a predefined time has elapsed since the start of the fourth step.

Figure 10:
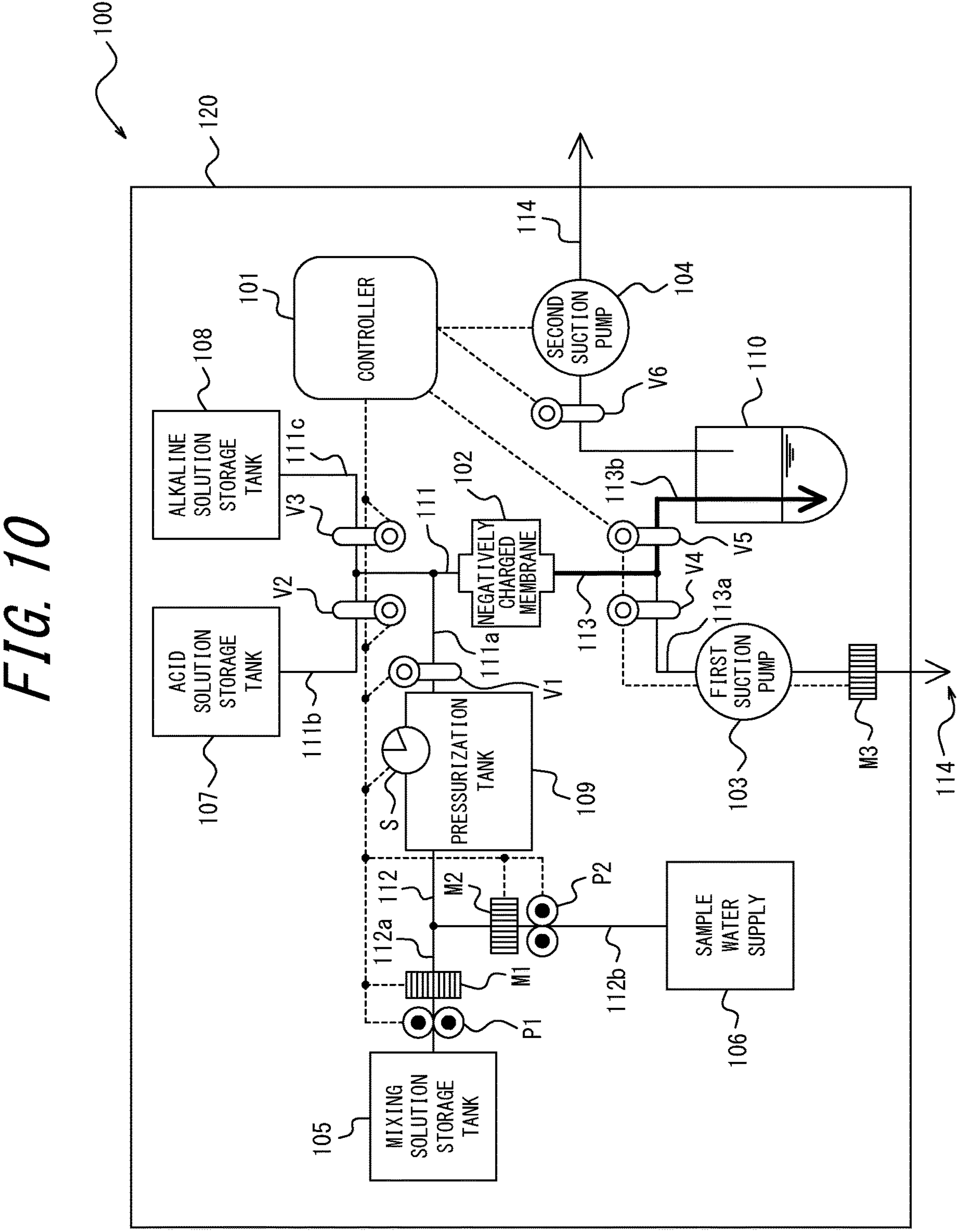
FIG. 10 is a schematic diagram for explanation of a fifth step of processing of the negatively charged membrane method executed by the concentration apparatus illustrated in FIG. 5.

FIG. 10 is a schematic illustration for explanation of the fifth step of the processing of the negatively charged membrane method executed by the concentration apparatus 100 illustrated in FIG. 5. In the fifth step, as illustrated in FIG. 11, the controller 101 opens the fifth solenoid valve V5 and closes the other solenoid valves. The controller 101 also causes the first pump P1, the second pump P2, the first flow meter M1 through to the third flow meter M3, the pressure sensor S, the first suction pump 103, and the second suction pump 104 to be stopped.

The inside of the concentrated solution collection vessel 110 is under negative pressure due to the fourth step, and therefore the opening of the fifth solenoid valve V5 causes the sodium hydroxide aqueous solution supplied to the negatively charged membrane 102 in the third step to be drawn into the concentrated solution collection container 110 along with the virus captured in the negatively charged membrane 102, and the concentrated solution of the virus is properly collected in the collection container. In this way, the processing of the negatively charged membrane method is executed and the concentrated solution of the virus in the sample water may be purified into the concentrated solution collection container 110.

Thus, in the concentration apparatus 100 according to the present embodiment, the controller 101 controls the opening and closing of the first solenoid valve V1 through to the sixth solenoid valve V6 to execute the processing according to the negatively charged membrane method. In other words, in the concentration apparatus 100, the processing according to the negatively charged membrane method is automated. This reduces the labor burden on workers when processing according to the negatively charged membrane method. For example, in the concentration apparatus 100, the controller 101 controls solenoid valves and various pumps to execute the processing according to the negatively charged membrane method, eliminating the need for workers to visually check or manually manipulate solution flow paths. This increases the convenience of processing by the negatively charged membrane method according to the concentration apparatus 100. Automation also reduces human error that may occur when workers perform operations and stabilizes the efficiency of recovery of bacteria, viruses, and other microorganisms at a certain level.

Further, the concentration apparatus 100 is configured as a single integrated device, and therefore may be transported to locations where executing the processing according to the negatively charged membrane method is necessary. In other words, the concentration apparatus 100 itself is portable. Therefore, by transporting the concentration apparatus 100, sample water may be collected and processed according to the negatively charged membrane method at various water treatment plant sites. This allows the concentration apparatus 100 to be transported to a location as required to execute the processing according to the negatively charged membrane method for various purposes, such as, for example, when there is an emergency, unusual situation, or temporary requirement to perform the processing. The concentration apparatus 100 may be transported to execute the processing according to the negatively charged membrane method even in environments where facilities for processing according to the negatively charged membrane method are not available. Thus, according to the concentration apparatus 100, the convenience of processing according to the negatively charged membrane method is increased. In particular, transportation is facilitated when the enclosure 120 has a handle or wheels.

The above embodiment describes an example in which the concentration apparatus 100 automatically controls purification of a concentrated solution of microorganisms such as bacteria and viruses, but the concentration apparatus 100 is equally applicable to particulate and colloidal dispersion systems that are negatively charged and suspended in a liquid.

The concentration apparatus 100 described above may be used in a variety of fields and applications. For example, the concentration apparatus 100 described above may be used to monitor water quality management and treatment performance of water treatment infrastructure such as water purification plants, sewage treatment plants, water reclamation facilities, and seawater desalination facilities. The concentration apparatus 100 described above may also be used, for example, to conduct dynamic surveys of the environment in water bodies such as rivers, oceans, water features, swimming pools, bathing areas, and the like. The concentration apparatus 100 described above may also be used, for example, for water quality testing to determine the risk of microbial infection in a city covering water bodies and environmental infrastructure. The concentration apparatus 100 described above may also be used for the purpose of qualitative risk, safety monitoring, or quality control of liquids used for beverages or in the production of processed foods, to quantify risk or to verify a comparison with a threshold value to determine safety. The concentration apparatus 100 described above may also be used for testing the quality of water for industrial, irrigation, and agricultural use. The concentration apparatus 100 described above may be used, for example, to manage qualitative risk, safety monitoring, or quality control of liquids used for temperature and humidity management, such as in mist spraying, humidification devices, or water sprinkling. The concentration apparatus 100 described above may also be used with respect to water for which the use of permanent water quality research facilities is restricted, such as water for emergency or disaster situations. The concentration apparatus 100 described above may also be used to test the quality of water used in vehicles or transportation systems with attached living facilities, such as campers, large buses, ships, submarines, aircraft, space stations, and the like. The concentration apparatus 100 described above may also be used for quality control testing of water related to medical care such as water used in pharmaceutical manufacturing, dialysis therapy, and the like.

The concentration apparatus 100 described above may further have a function to detect problems such as fluid leakage in the concentration apparatus 100, for example, by measuring the flow rate of sample water supplied from the sample water supply 106 and the flow rate of wastewater discharged from the outlet 114, and comparing these flow rates.

The concentration apparatus 100 described above may have a mechanism for automatically starting and stopping water sampling, such as a timer. The concentration apparatus 100 described above may also have a mechanism to start and stop water sampling by remote control. Thus, when the concentration apparatus 100 has a timer and remote control functions, the processing according to the negatively charged membrane method may be executed without requiring workers to be present at the site where the concentration apparatus 100 is active.

The present disclosure is not limited to the configuration specified in the embodiment described above, and various variations are possible without departing from the scope of the claims. For example, functions included in each component, each step, and the like may be reconfigured and multiple components or steps may be combined into one or divided, as long as no logical inconsistency results.

REFERENCE SIGNS LIST

1 Equipment
2, 102 Negatively charged membrane
3 Aspirator
4 Suction bottle
5, 11, 11*a*, 11*b*, 114 Pipe
5*a*, 111*a* First pipe
5*b*, 111*b* Second pipe
5*c*, 111*c* Third pipe
6 Sample water supply port
7, 107 Acid solution storage tank
8, 108 Alkaline solution storage tank
10, 110 Concentrated solution collection container
100 Concentration apparatus
101 Controller
103 First suction pump
104 Second suction pump
105 Mixing solution storage tank
106 Sample water supply
109 Pressurization tank
111 Upstream pipe
112 Mixing pipe
112*a* Fourth pipe
112*b* Fifth pipe
113 Downstream pipe
113*a* Sixth pipe
113*b* Seventh pipe
114 Outlet
120 Enclosure
M1 First flow meter
M2 Second flow meter
M3 Third flow meter
P1 First pump
P2 Second pump
S Pressure sensor
V1 First solenoid valve
V2 Second solenoid valve
V3 Third solenoid valve
V4 Fourth solenoid valve
V5 Fifth solenoid valve
V6 Sixth solenoid valve

The invention claimed is:

1. A concentration apparatus comprising:

a negatively charged membrane that is negatively charged;

a sample water supply disposed upstream of the negatively charged membrane and operable to supply sample water;

a first solenoid valve disposed on a flow path from the sample water supply to the negatively charged membrane;

an acidic solution storage tank disposed upstream of the negatively charged membrane in parallel with the sample water supply and storing an acidic solution;

a second solenoid valve disposed on a flow path from the acidic solution storage tank to the negatively charged membrane;

an alkaline solution storage tank disposed upstream of the negatively charged membrane in parallel with the sample water supply and the acidic solution storage tank and storing an alkaline solution;

a third solenoid valve disposed on a flow path from the alkaline solution storage tank to the negatively charged membrane;

an outlet disposed downstream of the negatively charged membrane and operable to discharge fluid externally;

a fourth solenoid valve and a first suction pump each disposed on a flow path from the negatively charged membrane to the outlet;

a collection container disposed downstream of the negatively charged membrane in parallel with the outlet and in which fluid is collected;

a fifth solenoid valve disposed on a flow path from the negatively charged membrane to the collection container; and a controller that controls opening and closing of the first solenoid valve, the second solenoid valve, the third solenoid valve, the fourth solenoid valve, and the fifth solenoid valve, wherein the controller is operable to execute a sequence of:

opening the first solenoid valve and the fourth solenoid valve, closing the second solenoid valve, the third solenoid valve, and the fifth solenoid valve, and causing the first suction pump to be driven;

opening the second solenoid valve and the fourth solenoid valve, closing the first solenoid valve, the third solenoid valve, and the fifth solenoid valve, and causing the first suction pump to be driven; and opening the third solenoid valve and closing the first solenoid valve, the second solenoid valve, the fourth solenoid valve, and the fifth solenoid valve.

2. The concentration apparatus of claim 1, further comprising a mixing solution storage tank disposed upstream of the first solenoid valve in parallel with the sample water supply that stores a mixing solution to be mixed with the sample water.

3. The concentration apparatus of claim 2, further comprising:

a first pump operable to pump the mixing solution downstream; and a second pump operable to pump the sample water downstream, wherein the controller controls the pumping by the first pump and the second pump.

4. The concentration apparatus of claim 1, further comprising a pressurization tank upstream of the first solenoid valve that stores the sample water supplied from the sample water supply.

5. The concentration apparatus of claim 1, further comprising a second suction pump operable to create negative pressure inside the collection container.

6. The concentration apparatus of claim 5, wherein the controller is operable to execute a sequence of:

a fourth step of closing the fifth solenoid valve and causing the second suction pump to be driven to create negative pressure inside the collection container; and a fifth step of closing the first solenoid valve, the second solenoid valve, the third solenoid valve and the fourth solenoid valve, and opening the fifth solenoid valve.

7. The concentration apparatus of claim 1, wherein the concentration apparatus is configured as one integrated device.

8. The concentration apparatus of claim 7, wherein the concentration apparatus is configured as an integrated device by being entirely housed inside an enclosure.

9. The concentration apparatus of claim 8, wherein the enclosure is provided with a handle that is graspable by a user.

10. The concentration apparatus of claim 1, wherein the concentration apparatus further comprises wheels.

11. A concentration method executed by a concentration apparatus comprising:

a negatively charged membrane that is negatively charged;

a sample water supply disposed upstream of the negatively charged membrane and operable to supply sample water;

a first solenoid valve disposed on a flow path from the sample water supply to the negatively charged membrane;

an acidic solution storage tank disposed upstream of the negatively charged membrane in parallel with the sample water supply and storing an acidic solution;

a second solenoid valve disposed on a flow path from the acidic solution storage tank to the negatively charged membrane;

an alkaline solution storage tank disposed upstream of the negatively charged membrane in parallel with the sample water supply and the acidic solution storage tank and storing an alkaline solution;

a third solenoid valve disposed on a flow path from the alkaline solution storage tank to the negatively charged membrane;

an outlet disposed downstream of the negatively charged membrane and operable to discharge fluid externally;

a fourth solenoid valve and a first suction pump each disposed on a flow path from the negatively charged membrane to the outlet;

a collection container disposed downstream of the negatively charged membrane in parallel with the outlet and in which fluid is collected; and a fifth solenoid valve disposed on a flow path from the negatively charged membrane to the collection container, the concentration method comprising:

a first step of opening the first solenoid valve and the fourth solenoid valve, closing the second solenoid valve, the third solenoid valve, and the fifth solenoid valve, and causing the first suction pump to be driven;

a second step of opening the second solenoid valve and the fourth solenoid valve, closing the first solenoid valve, the third solenoid valve, and the fifth solenoid valve, and causing the first suction pump to be driven; and a third step of opening the third solenoid valve and closing the first solenoid valve, the second solenoid valve, the fourth solenoid valve, and the fifth solenoid valve.

* * * * *